United States Patent [19]
Hluchy

[11] Patent Number: 5,716,354
[45] Date of Patent: Feb. 10, 1998

[54] ENDOSCOPIC INSTRUMENT WITH ROTATABLE INSTRUMENT COUPLING

[75] Inventor: Heinz Hluchy, Hamburg, Germany

[73] Assignee: Olympus Winter & Ibe GmbH, Hamburg, Germany

[21] Appl. No.: 626,811

[22] Filed: Apr. 2, 1996

[30] Foreign Application Priority Data

Apr. 5, 1995 [DE] Germany ............... 195 12 640.8

[51] Int. Cl.$^6$ ............................................. A61B 17/36
[52] U.S. Cl. ............................................. 606/46
[58] Field of Search ........................... 606/46, 51, 52

[56] References Cited

U.S. PATENT DOCUMENTS

| | | | |
|---|---|---|---|
| 4,003,380 | 1/1977 | Wien | 606/51 |
| 5,569,243 | 10/1996 | Kortenbach et al. | 606/51 |

FOREIGN PATENT DOCUMENTS

| | | | |
|---|---|---|---|
| 537 574 | 4/1993 | European Pat. Off. | |
| 596 436 | 5/1994 | European Pat. Off. | |
| 93 17 664.3 | 1/1994 | Germany | |

*Primary Examiner*—William E. Kamm
*Assistant Examiner*—George R. Evanisko
*Attorney, Agent, or Firm*—Walter C. Farley

[57] ABSTRACT

A surgical endoscopic instrument has a stem portion and a handle portion and an operating insert axially extending through both of those portions. The insert carries at least one hf operating electrode which can project beyond the distal end of the stem portion. An insulated electrical conductor extends along the length of the operating insert to connect the electrode to a plug subassembly forming the proximal end of the operating insert. The plug subassembly is electrically connected to a removable jack with a connection cable leading to an hf energy source. The operating insert is rotatably supported inside the implement and the jack is non-rotatably coupled to the plug subassembly which is itself non-rotatably linked to the operating insert.

4 Claims, 1 Drawing Sheet

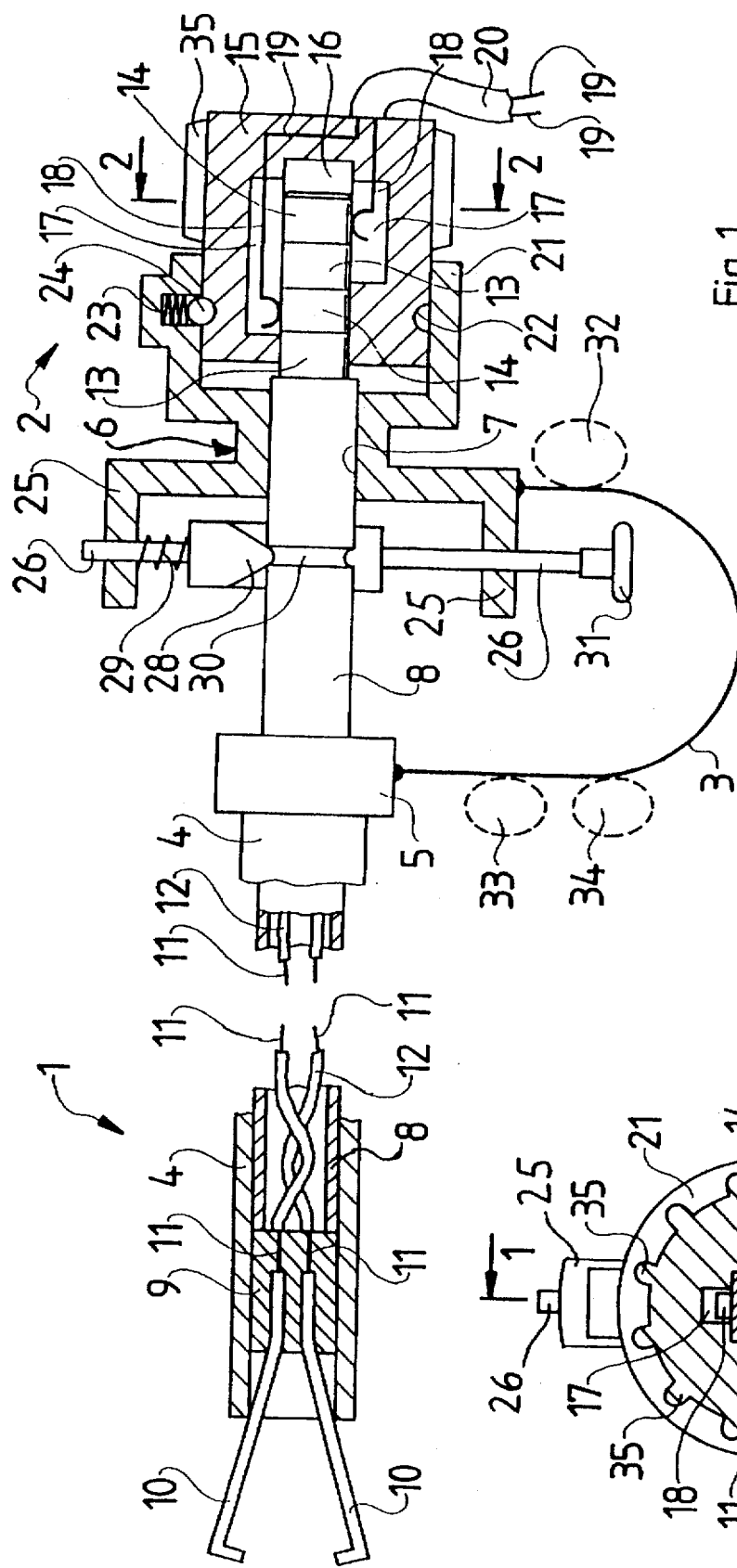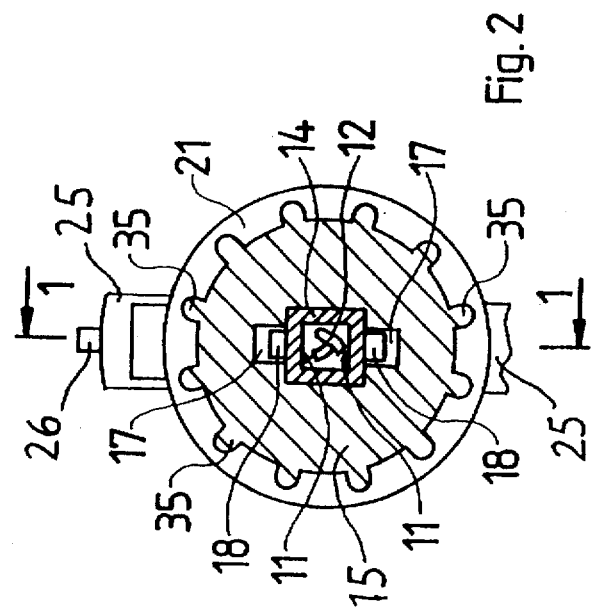

ENDOSCOPIC INSTRUMENT WITH ROTATABLE INSTRUMENT COUPLING

FIELD OF THE INVENTION

This invention relates to an endoscopic instrument having a high-frequency electrode with control means for selectively supplying high frequency electrical energy to the electrode.

BACKGROUND OF THE INVENTION

Surgical implements with operating electrodes are used in all endoscopic interventions, in particular in laparoscopy. As a rule, they are inserted by a long stem member through an endoscope duct already in place in the body of a patient and serve to cut tissue by application of high-frequency (hereafter "hf") energy.

The electrodes may assume the shapes of blades or plates and frequently are in the form of cutting hooks. So-called bipolar devices also are widely used, the surgery taking place with two cutting electrodes which, typically, are manually and mutually displaceable in the manner of tongs, these electrodes being connected to the two terminals of an hf generator which supplies hf current between the two terminals. Such implements also are called bipolar tongs and illustratively are used in uterine-tube suppression.

During surgery, implements of this general type must be used at various angles of rotation, depending on the required direction of cutting. In the case of bipolar tongs, sometimes they must be rotated in such a way as to be operating perpendicularly to the uterine tube. The implement must then be rotated constantly. This feature however is a drawback, because the conventional design of such implements offers a reliable grip of the surgeon's hand on the driving component only in a given direction. Accordingly, the surgery takes place with the hand in a disadvantageous, clumsy position, or the hand location must be changed during a surgical procedure, a very undesirable necessity.

Rotatable, operative inserts cannot be used on such implements to solve the above problem, because economical and simple implements of this design of the state of the art lack the ability to rotate.

Implements are known which rotatably support the operative electrode and which are driven by means of a rotary grip.

Such an implement is disclosed in European patent document 0,537,574 A2. It requires a separate rotary grip and a special eccentric mounting of the electrode connector. Accordingly, the implement is comparatively complex and susceptible to difficulties.

German patent document U1 39 17 664 discloses an implement wherein an electrical connector is mounted directly at the proximal end of an operating electrode. This operating electrode is rotated by a rotary grip which drives a stem tube enclosing the operating electrode at the far distal end, the tube being non-rotatably coupled to the operating electrode and thereby rotating it. Accordingly, the operating electrode is rotatably contacted by the electrical connector. This design also is unusually complex.

European patent document 0 596 436 A1 discloses an implement in which a rotary grip drives the operating electrode at its proximal end. At that location, the electrical connector is non-rotatably seated on the operating electrode and moreover it is also non-rotatably connected to the rotary grip. In this configuration therefore the connector non-rotatably couples the operating electrode and the rotary grip. Again this design is highly complex.

SUMMARY OF THE INVENTION

An object of the present invention is to provide an economical endoscope which also evinces a simple configuration.

Briefly described, the invention comprises a surgical endoscopic instrument having a stem portion, a handle portion and an operational insert having at least one high-frequency energized operating electrode movable to project beyond a distal end of the stem portion. A plug subassembly forms the proximal end of the operating insert. A removable jack is connected to a connecting cable and electrically coupled to the plug subassembly. Insulated electrical conductors electrically connect the electrode through the length of the operating insert to the plug subassembly. The operating insert is rotatably supported inside the endoscope, the jack being non-rotatably connected to the plug subassembly and the plug subassembly being non-rotatably coupled to the operating insert, and the jack forming a rotary grip Compared to known instruments for similar purposes, the present invention is characterized by substantially enhanced simplicity. The electrical connector itself is made to be the rotary grip. Therefore the separately provided rotary grip of the prior art may be omitted and hence also the complex rotary coupling between the electrical connector and the rotary grip. The configuration is much simplified thereby and, surprisingly, handling is also improved, because the electrical connector, which is located on the proximal side, can be better gripped by one hand while the implement is held by the other hand than can the rotary grip farther to the fore, that is farther distally.

By rotatably linking the operating insert to the handling portion with a disengageable stop, the operating insert may be changed merely by pulling it out of the implement, for instance in case of wear or defective insulation, or to exchange it with other operating inserts for special applications that use cutting electrodes of other shapes.

By rotatably linking the jack to the handling portion with a disengageable stop which is axially stationary, undesired disengagement of the electrical contacts during surgery is prevented.

By shaping the jack as a rotary member with corrugations in a proximal segment freely projecting beyond the handling portion, manual rotation is facilitated.

BRIEF DESCRIPTION OF THE DRAWINGS

The invention is illustratively and schematically shown in the accompanying drawings wherein:

FIG. 1 is an axial section along line 1—1 of FIG. 2 through bipolar tongs of the invention; and FIG. 2 is a transverse section along line 2—2 of FIG. 1 through the electrical connector.

DESCRIPTION OF THE PREFERRED EMBODIMENTS

The figures show bipolar tongs with a stem portion indicated generally at 1 and a handle portion indicated generally at 2 for manipulating the instrument. These portions are interconnected by a bent leaf spring 3 of a preselected width which is attached to the stem and handling portions 1 and 2 such that these portions are longitudinally linked by the spring but are not rotatable relative to each other. Conventional slide guides for axial alignment and for preventing rotation between the stem and handling portions 1 and 2 are omitted for clarity from the drawing.

The stem portion 1 comprises an insulated (i.e., electrically non-conductive) stem tube 4 affixed to the proximal end of a slidable part 5 supporting the distal end of the leaf spring 3.

Handle portion 2 comprises a housing 6 having an axial and continuous borehole 7 therethrough, the inner diameter of which corresponds to the inner diameter of stem tube 4 with which it is flush and coaxially aligned. The proximal end of leaf spring 3 is attached to housing 6.

An operating implement with a sheath tube 8 passes through and is rotatably supported in the stem and handle portions 1 and 2. Tube 8 illustratively may be metallic for strength. An insulator 9 is at the distal end of, and within, sheath tube 8 and houses, for example in a potting material, the proximal ends of two resilient tong electrodes 10.

Tong electrodes 10 are electrically connected within insulator 9 to electrical conductors 11 clad with electrical insulation 12 and passing through the length of sheath tube 8.

An electrical connector comprising two longitudinally separated tubular insulators 13 and two electrically conductive tubular contacts 14, separated from each other by the insulators, projects proximally beyond the distal end of sheath tube 8. As shown in the sectional view of FIG. 2, the ends of electrical conductors 11 are exposed and each conductor is electrically connected to one of contacts 14 on the inside of the tubular connector.

Insulators 13 and contacts 14 are cross-sectionally identical to form a first connector similar to a telephone plug somewhat smaller in diameter than sheath tube 8 and being of a non-circular cross-section, for instance square in the embodiment shown in FIG. 2.

Electrical connector 13, 14 so formed is connected to a second connector or jack 15 and is non-rotatably seated therein by a mating square axial recess 16 on the plug sub-assembly. Jack 15 receives two contact springs 18 in slots 17 adjoining the recess 16, each spring resting in electrically contact with one of contacts 14. Contact springs 18 pass through the proximal end of insulating jack 15 and are connected to electrical conductors 19 of a connecting cable 20 connected to jack 15, the cable in turn leading to an hf generator, not shown.

To ensure reliable guidance and protection against kinking or breaking of the connector, jack 15 is rotatably supported at its distal end in a concentric annular wall 21 of housing 6 (FIG. 1). In that region, jack 15 has an external circumferential groove 22 engaged by a locking ball 24 radially displaceable inside annular wall 21 and pressed inward by a spring 23, forming a detent structure for permitting rotation but inhibiting relative axial motion.

Disengageable stop means coupling sheath tube 8 to the handle portion includes a stop blade 28 held transversely to the endoscope axis by pins 26 in arms 25 mounted distally of housing 6 and urged by a spring 29 into an annular channel 30 on sheath tube 8, the tube thereby being kept stationary in the axial direction while still being rotatable.

After jack 15 has been removed and stop blade 28 has been released by depressing a knob 31 at the end of one of pins 26, the operating device can be replaced by another by being pulled out of stem portion 1.

Following insertion of a stem portion and slipping jack 15 onto the jack sub-assembly 13, 14, the implement is ready for operation.

The surgeon grasps handle portion 2 at leaf spring 3, using his thumb 32, index finger 33 and middle finger 34, and then, by compressing the ends of leaf spring 3 toward each other, he can displace shaft portion 1 in the direction of handle portion 2 within which the operating instrument together with its sheath tube 8 is held axially stationary. As a result, the distal end of the stem tube 4 moves toward the resilient and spaced-apart tong electrodes 10 which it forces together into various angular positions relative to each other.

If the tong electrodes 10 are in a circular angular position other than desired relative to the instrument position, i.e., relative to a vertical plane through the instrument axis, then the surgeon seizes with his other hand jack 15 which has corrugations 35 on the outer surface of its end proximally projecting beyond annular wall 21, forming a rotatable grip. By means of the cross-sectional locking between recess 16 of jack 15 and plug sub-assembly 13, 14, he rotates sheath tube 8 non-rotatably joined to that sub-assembly, so that the tong electrodes 10 non-rotatably linked to tube 8 are also rotated into the desired circular position.

It should be noted that the instrument of the invention is for use with an endoscope or with a tubular device similar to an endoscope in which the optics may be separately housed.

The scope of the invention allows many instrument variations. The implement may be unipolar, that is comprising only one, illustratively hook-shaped cutting electrode. The remaining design may be identical. Thereby the plug subassembly is simplified by only one contact 14 being required. Jack 15 also is commensurately simplified. In such an implement, the longitudinal displaceability between shaft portion 1 and handle portion 2 may be eliminated. These portions may be connected to each other.

The non-rotatable coupling of jack 15 to the plug subassembly 13, 14 may be achieved in another way. For example, in a bipolar implement as shown in the Figures, the two contacts may be mounted in axially parallel manner, similarly to a household outlet, rather than being axially consecutive as the shown contacts 14. This design also secures mutual non-rotatability of the components.

The electric connection also may be implemented in a manner similar to that shown but wherein the plug subassembly evinces circular cross-sections of its parts 13 and 14 with longitudinal flutings or the like which are engaged by corresponding locking means for jack 15, for instance the contact springs 18, to assure non-rotatability. The structure also may be arrange such that, in the presence of excessive torques, there will be rotational-stress relief by the springs yielding elastically.

What is claimed is:

1. A surgical endoscopic instrument comprising:
   a stem portion (1);
   a handle portion (2);
   an operational insert (8, 10) comprising at least one high-frequency energized operating electrode (10) movable to project beyond a distal end of said stem portion (1);
   a first connector subassembly (13, 14) forming a proximal end of said operating insert;
   an electrical cable;
   a second connector (15) connected to said cable and electrically coupled to said first connector subassembly, said second connector being removable from said first connector subassembly;
   insulated electrical conductor means (11) for electrically connecting said electrode (10) through the length of said operating insert to said first connector subassembly (13, 14);

said operating insert (10, 8) being rotatably supported inside said endoscopic instrument (1, 2);

said second connector (15) being non-rotatably connected to said first connector subassembly (13, 14);

said first connector subassembly being non-rotatably coupled to said operating insert (8); and said second connector (15) having a rotatable grip, whereby said operating insert can be rotated relative to said handle portion for angularly positioning said electrode.

2. An endoscopic instrument according to claim 1 and comprising disengageable stop means (28, 30) for rotatably coupling said operating insert (8, 10) to said handle portion, said stop means (28, 30) preventing axial relative motion thereof.

3. An endoscopic instrument according to claim 1 and further comprising a releasable detent (22, 24) for rotatably coupling said second connector (15) to said handle portion while inhibiting relative axial motion thereof.

4. An endoscopic instrument according to claim 1, wherein said rotatable grip of said second connector (15) comprises a proximal segment having an outer grip surface with corrugations (35), said segment projecting beyond said handle portion (2).

* * * * *